United States Patent [19]

Asher et al.

[11] 4,183,918

[45] Jan. 15, 1980

[54] DETOXIFYING-MEDICINAL EMULSIONS

[75] Inventors: William J. Asher, Fanwood; Norman N. Li, Edison; Adam L. Shrier, Montclair, all of N.J.

[73] Assignee: Exxon Research & Engineering Co., Florham Park, N.J.

[21] Appl. No.: 877,340

[22] Filed: Feb. 13, 1978

Related U.S. Application Data

[63] Continuation of Ser. No. 775,575, Mar. 8, 1977, abandoned, which is a continuation-in-part of Ser. No. 466,293, May 2, 1974, abandoned.

[51] Int. Cl.$^2$ .................... A61K 37/48; A61K 47/00; A61K 33/08
[52] U.S. Cl. .................................. 424/94; 424/127; 424/154; 424/358; 424/365
[58] Field of Search ................. 424/94, 365, 127, 154, 424/358

[56] References Cited

U.S. PATENT DOCUMENTS 4,115,313  9/1978  Lyon et al. ........................... 424/365

FOREIGN PATENT DOCUMENTS 4234  7/1968  South Africa.

*Primary Examiner*—Sam Rosen
*Attorney, Agent, or Firm*—Joseph J. Allocca

[57] ABSTRACT

This invention relates to the use of liquid membrane technology in preparing medicinals. The medicinals prepared by this invention may be ingested and may be utilized as traps for toxins present in the GI (gastrointestinal) tract, or as slow-release compositions of drugs, or as reactors. In the trap embodiment, the liquid membrane encapsulated medicinal is an emulsion comprising an exterior phase which is immiscible with the liquids present in the GI tract and permeable to the toxins therein, and an interior phase which is immiscible with the exterior phase and comprises a reagent capable of converting said toxin into a nonpermeable form. In addition, hydrophilic adsorbents, such as a hydrophilic carbon or a silica gel, may be encapsulated in the emulsions of the instant invention. When the compositions of the instant invention are utilized as slow-release drugs, the interior phase of the emulsion will comprise a drug which is slightly soluble in the exterior phase of the emulsion whereby said drug permeates through said exterior phase of the emulsion over a period of time into the GI tract. The third method for utilizing the compositions of the instant invention comprises encapsulating a catalyst for a reaction which is desired to be carried out in the GI tract. In this embodiment the reactants present in the GI tract permeate through the exterior phase of the emulsion into an interior phase wherein said catalyst, for example, an enzyme, converts the permeated reactants to reaction products. The reaction products then may permeate through the exterior phase back into the GI tract. In all cases, the liquid membrane encapsulated medicinals may be administered by either oral ingestion or injection anywhere else into the GI tract.

69 Claims, No Drawings

DETOXIFYING-MEDICINAL EMULSIONS

CROSS-REFERENCE TO RELATED APPLICATIONS

This application is a Continuation Under Rule 60 of application Ser. No. 775,575 filed Mar. 8, 1977 (now abandoned) which was a continuation-in-part of application Ser. No. 466,293 filed May 2, 1974 (now abaondoned).

BRIEF DESCRIPTION OF THE INVENTION

This invention relates to the use of liquid membrane technology in preparing medicinals. The medicinals prepared by this invention may be ingested and may be utilized as traps for toxins present in the GI (gastrointestinal) tract, or as slow-release compositions of drugs, or as reactors. In the trap embodiment, the liquid membrane encapsulated medicinal is an emulsion comprising an exterior phase which is immiscible with the liquids present in the GI tract and permeable to the toxins therein, and an interior phase which is immiscible with the exterior phase and comprises a reagent capable of converting said toxin into a nonpermeable form. In addition, hydrophilic adsorbents such as a hydrophilic carbon or a silica gel may be encapsulated in the emulsions of the instant invention. When the compositions of the instant invention are utilized as slow-release drugs, the interior phase of the emulsion will comprise a drug which is slightly soluble in the exterior phase of the emulsion whereby said drug permeates through said exterior phase of the emulsion over a period of time into the GI tract. The third method for utilizing the compositions of the instant invention comprises encapsulating a catalyst for a reaction which is desired to be carried out in the GI tract. In this embodiment the reactants present in the GI tract permeate through the exterior phase of the emulsion into an interior phase wherein said catalyst, for example, an enzyme, converts the permeated reactants to reaction products. The reaction products then may permeate through the exterior phase back into the GI tract. In all cases the liquid membrane encapsulated medicinals may be administered by either oral ingestion or injection anywhere else into the GI tract.

SUMMARY OF THE PRIOR ART

It is known in the art that solid microcapsules may be utilized to encapsulate medicinals. For example, in the Dec. 20, 1971 issue of "The Journal of the American Medical Association" in the "Medical News Section", a review of the microencapsulated medicinal art is presented. In this article, a technique for treating uremic wastes in the gastrointestinal tract with microencapsulated activated carbon is disclosed. The microcapsule is permeable to the uremic wastes and said activated carbon is utilized to absorb some of the wastes. In this technique, uric acid and creatinine are removed. The above reference also teaches a technique wherein urea is converted to ammonia and $CO_2$ by the use of microencapsulated urease. The ammonia is then reacted with and trapped by a microencapsulated ethylene maleic acid copolymer while the carbon dioxide is exhaled through the lungs.

It is known in the art of slow-release medicinals that medicinals can be encapsulated by various solid materials, for example, hydroxy alkyl cellulose ethers, as taught in U.S. Pat. No. 3,493,407, and gelatin, as taught in U.S. Pat. No. 3,526,682. In both of these patents, the microencapsulated medicinal is released over a time period into the GI tract by dissolution of the solid capsule material.

There are various problems known in the art in using solid microcapsules as reactors, as traps and as slow-release compositions. One problem is that solid capsules are prone to swell followed by rupture. Various methods to solve this problem have been utilized, including crenation, etc. Crenation increases the cost of microencapsulated systems and when long residence time in the GI tract are encountered, these compounds or compositions still rupture to an undesirable extent. Furthermore, the microencapsules which do not dissolve in the tract often lead to fecal compaction. In the compositions of the instant invention, the encapsulating media is liquid; thus expansion of the internal phase does not lead to rupture of the composition as in the solid microencapsulated system disclosed above.

As pointed out in the patents cited above, when gelatin is utilized to encapsulate medicinals to provide slow release, various conditions encountered during storage can affect the rate of release in the GI tract; for example, gelatin is very sensitive to temperature and humidity, etc. In the emulsion systems of the instant invention, storage conditions do not substantially affect the rate of release of the compositions in the GI tract.

U.S. Pat. No. 3,538,216 describes an invention in which a thixotropic or gelatinous oil containing a drug for sustained release is injected into an animal. The instant invention is quite different in that a suspendable emulsion is ingested.

The prior art has also utilized medicinal compositions encapsulated in liposomes, for example, in the Apr. 20, 1973 issue of "Science" (Vol. 180, pp 300–301), Yueh-Erh Rahman et al encapsulated chelating agents in liposomes. There are quite a few differences between liposome encapsulation and the instant invention. The liposome compositions in the above-cited article are introduced into the body by injection rather than orally. This is in direct contrast to the oral ingestion of the emulsions of the present invention. Further, liposomes differ both structurally and operationally from the instant invention. Liposomes consist of alternating concentric layers of liposomes and aqueous phase (cf. "New Scientist", Dec. 27, 1973, at p. 891). Liposomes function—that is, release their contents—only by the rupture of these layers (cf FEBS LETTERS, Vol. 36, No. 3, November, 1973, at page 295). On the other hand, the emulsions of the instant invention do not consist of multiple concentric layers of liposomes and water, but consist of an exterior oil phase (which contains an oil component and an oil-soluble surfactant component) and an aqueous interior phase (which contains various reactants or medicinal compounds). Further, unlike the liposome encapsulated compositions, the emulsions of the instant invention do not release their encapsulated medicinals by rupture. The emulsions of the instant invention operate by permeation through the exterior phase, i.e. the exterior phase of the instant invention remains intact. Finally, liposomes cannot be utilized to remove substances present in the GI tract by capturing the substances through permeation of its concentric layers. By contrast, the emulsions of the instant invention can be utilized to remove substances in the GI tract. This capture is accomplished by the permeation of the substance through the exterior phase into the interior phase where it is converted to a nonpermeable form.

In summary, liposome encapsulation differs from the instant invention in the following respects: it is a composition that (i) is introduced into the body by injection rather than oral ingestion, (ii) is structurally and operationally different from the present invention, and (iii) may not be applied to processes in which the present invention is utilized.

Finally, the present invention also differs from the emulsions of the prior art typified by those of U.S. Pat. Nos. 2,322,822. U.S. Pat. No. 2,322,822 teaches water-in-oil emulsions that may be formed utilizing countless oils and surfactants enumerated therein resulting in innumerable combinations. This reference, however, does not differentiate between any of the oils or the surfactants listed, regarding them all as equivalents. Specifically, U.S. Pat. No. 2,322,822, starting at column 2, line 47 and ending at column 3, line 4, lists groups of oils which inlcude animal and vegetable oils. The teaching of the instant invention specifically rejects the equivalency of potential oil components which include animal and vegetable oils. The present invention teaches that many of the animal and vegetable oils cannot be used to form the compositions of the instant invention since these oils are readily digested. Thus, the instant invention, unlike the prior art, teaches the nonequivalence and unique characteristic of specific oil components that will form emulsions that will remain stable in the GI tract.

Similarly, as U.S. Pat. No. 2,322,822 teaches the equivalence of surfactants (column 3, lines 14–24), the instant invention teaches the nonequivalence. The present invention places limitations upon the surfactant component not required by the prior art, i.e. that the surfactant be harmless for internal use and that such surfactant be utilized to form emulsions which remain intact in the GI tract.

To summarize, the prior art does not properly distinguish between the potential oil and oil-soluble surfactant components in order to form the limited type of emulsions that exhibit those specialized characteristics for use in the GI tract—permeability and stability—as is done by the instant invention.

DETAILED DESCRIPTION OF THE INVENTION

The instant invention relates to medicinal compositions which comprise a medicinal emulsified in a water-immiscible exterior phase. The emulsion is designed to be stable during passage through the GI tract where said medicinals will be utilized. To prepare the composition of the instant invention, the medicinal is normally dissolved in a medium, usually aqueous, and the solution thereof is emulsified in an oil-containing phase, which phase is immiscible with the liquids present in the GI tract. The oil phase would generally contain an oil-soluble surfactant to enable the preparation of an emulsion which will be stable during passage through the GI tract. The exterior phase of the emulsion thus acts like a liquid membrane surrounding the interior phase.

In a preferred embodiment, the emulsion described above is further dispersed in a liquid which is immiscible with the exterior phase of the emulsion, for example, water. This preferred embodiment allows the use of the compositions of the instant invention in a form wherein dispersion of the emulsion in the GI tract is increased. Furthermore, because of the well-known unpalatability of the usual oils which are used to form the emulsions of the instant invention, the continuous phase comprising water or water and flavoring agents is desirable.

The compositions of the instant invention can be utilized in at least three different manners. For example, to remove toxins, reactants and adsorbents can be emulsified in the interior phase of an emulsion. The exterior phase of this emulsion will be designed to allow the toxins present in the GI tract to permeate through and react with the reactant or be adsorbed on the absorbent present in the interior phase of the emulsion. In this manner, toxins are continuously and irreversibly removed as the emulsion passes through the GI tract. In this embodiment, the membrane is designed to be impermeable to the reaction products or adsorbed products formed in the interior phase of the emulsion.

In an alternate method, the liquid membrane is utilized to encapsulate catalysts which will be used in carrying out reactions while passing through the GI tract. The catalyst may be, for example, an enzyme, e.g. urease. The liquid membrane encapsulating the catalysts can effectively protect the catalyst from the environment of the GI tract. Particularly, the catalyst itself can be used under conditions where the catalyst in an unencapsulated state would be destroyed. For example, urease could be protected from the low pH present in the stomach of the GI tract by designing the liquid membrane to exclude the passage of ions including hydrogen ion.

In the third use of the compositions of the instant invention, medicinals are released by permeating through the exterior phase of the emulsion into the GI tract during the passage of the emulsion through the GI tract. In this embodiment, the medicinal compound is emulsified in a liquid in which the medicinal is only sparingly soluble. This low solubility in the exterior phase of the emulsion allows passage of the medicinal into the GI tract over long time periods.

In preparing the compositions of the instant invention, it is desirable that the exterior phase of the emulsion be made up of an oil component and an oil-soluble surfactant component. The oil, of course, is designed to be immiscible with the liquids present in the GI tract. The oil component and the oil-soluble surfactant component must not be harmful to the human body. For example, as is known in the art, certain types of polynuclear aromatic oils are harmful to the human body. Therefore, these oils cannot be utilized with the instant invention. Further, the oil component along with the oil-soluble surfactant component should also be fairly inert so that they are not destroyed by the environment in the GI tract.

The body digests many of the natural animal and vegetable oils. These readily digested oils such as triglycerides cannot be used to form a large fraction of the oil in the external phase. The natural digestive processes would be expected to remove these oils from the emulsion as it passed through the GI tract.

It is well known in the art that "most artificial or natural emulsions are broken in the stomach". See, for example, *Physiology of the Digestive Tract*, H. W. Davenport, 3rd Ed. 1971 Year Book Medical Publishers, Inc., Chicago, Ill., page 197. It takes a special type of emulsion composition to pass through the GI tract intact. Some examples of oils which could be utilized in forming the compositions of the instant invention include hydrocarbon oils that are refined to remove toxic ingredients and comprise molecular weights up to 1,000, e.g. paraffins, isoparaffins, naphthenes and aromatics. Particularly desirable are the mineral oils which have been highly refined for use in human ingestion. Additionally, oils or treated oils from animal or vegetable sources may be used if they can pass through the GI tract substantially unconverted, for example, vegetable oils and animal fats that are heavily hydrogenated to contain at least 10 wt. % more hydrogen than at normal saturation. Further silicone fluids containing the repeating unit

can be used. Perflluorinated hydrocarbons may also be used. Any of these oils should have a viscosity of about 2 to about 1000 centistokes at normal body temperature. The preferable range is about 10 to about 150 centistokes.

As noted above, the oil-soluble surfactant component must possess certain characteristics to be compatible with the instant invention. For instance, the oil-soluble surfactant component must not be harmful to the human body. Further, the oil-soluble surfactant component along with the oil component should also be fairly inert so as not to be destroyed by the environment of the GI tract. Nonionic surfactants that possess these required characteristics are the preferred surfactant type for the practice of the instant invention. A surfactant is nonionic if it does not ionize when added to the phase that will be the surfactant-containing phase, here, the oil phase.

Examples of oil-soluble surfactants possessing the desired characteristics include sorbitan monooleate and other types of sorbitan fatty acid esters, e.g., sorbitan, sorbitan-monolaurate, sorbitan monopalmitate, sorbitan stearate, sorbitan tristearate, sorbitan trioleate, polyoxyethylene sorbitan fatty acid esters, and mono- and diglycerides.

The oil-soluble surfactant component may be present in the exterior phase from about 0.01 wt. % up to the solubility of said surfactant in said exterior phase but not more than about 90 wt. % of said exterior phase. Preferably, the oil-soluble surfactant will be present in said exterior phase from about 0.01 wt. % up to the solubility limit of said surfactant in said exterior phase but not more than about 10 wt. % of said exterior phase. Most preferably, the oil-soluble surfactant will be present in the exterior phase from about 1 to about 5 wt. %., but in no case more than the solubility limit of a particular surfactant in the exterior phase.

It may also be desirable to use strengthening agents to improve the stability of the emulsions. Nonlimiting examples of strengthening agents include: polyisobutylene, i.e. especially the lower molecular weights, e.g. a molecular weight of about 900, polyisobutylene succinic anhydride-pentaerythritol adducts, ethylene-vinyl acetate copolymers, sulfonated butyl rubber and decylmethacrylatevinyl pyridine copolymers.

A preferred strengthening agent comprises a polyamine derivative having the general formula:

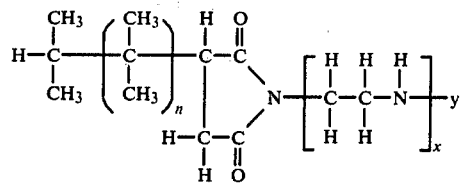

where n varies from 10 to 60, x varies from 3 to 10, and y is selected from the group consisting of hydrogen and oxygen-containing hydrocarbyl radicals having up to 10 carbons.

It should also be noted that the above class of polyamine derivatives are useful as surfactants and are preferred surfactants for the instant invention. When embodiments of the instant invention utilize these polyamine derivatives in the dual capacity of a surfactant and strengthening agent, the usable amounts of these polyamine derivatives are adjusted accordingly. Specifically, the upper wt. % limit for the polyamine derivatives used in the dual capacity is the combined upper weight percentage limits of a surfactant and a strengthening agent when two separate components are used. For example, if the upper weight limit for the surfactant is 10% in the exterior phase and the upper weight limit of the strengthening agent is also 10%, the polyamine derivative can be used up to 20 wt. % in the exterior phase.

A preferable amount of strengthening agent utilized in conjunction with the instant invention ranges from about 2 wt. % of said exterior phase up to the solubility limit of said strengthening agent in said exterior phase. Most preferably, the amount of strengthening agent ranges from about 2 wt. % of said exterior phase to about 5 wt. % of said exterior phase but in no case above the solubility limit of the particular strengthening agent.

EXAMPLE 1

A controlled release medicinal (sodium salicylate.)

In Experiment 1, a solution of 8 wt. % sodium salicylate and 8 wt. % sucrose in distilled water was used to form the interior phase of the emulsion. Experiment 2 used 10 wt. % sodium salicylate and 8 wt. % sucrose in water, but was the same as experiment 1 in all other respects.

These interior phases were added with vigorous agitation, in an amount sufficient to form 33 wt. % of the final emulsion, to an exterior phase (oil phase) consisting of:

2.0 wt. % Sorbitan monooleate 0.5 wt. % of a high molecular weight polyamine with the structure:

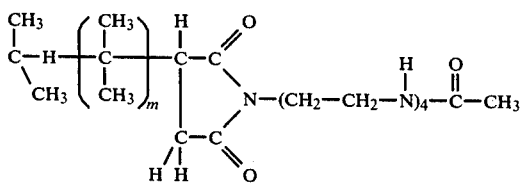

wherein m
is an integer of about 40
3.5 wt. % of a polyisobutylene with a molecular weight of about 900

94.0 wt. % of an isoparaffinic lubricating oil stock with a viscosity at 100° F. of about 100 Saybolt Universal seconds.

200 grams of this emulsion was suspended in 600 grams of a synthetic gut fluid which comprised:

0.8 wt. % albumin from eggs
0.5 wt. % NaCl
0.4 wt. % $NaHCO_3$
98.3 wt. % distilled water with mild agitation to simulate conditions in the small intestine. The appearance of sodium salicylate and sucrose in the bulk synthetic gut fluid were monitored with time by analysis. The results are shown in Table 1 below:

TABLE 1

Controlled Release of Medicinals (Sodium Salicylate) by Diffusion in Liquid Membrane

| Time Hrs. | Concn. in External Phase, % (1) | | % of Max.Equilibrium Concn. in Outer Phase | |
|---|---|---|---|---|
| | Sodium Salicylate | Sucrose | Sodium Salicylate | Sucrose |
| Expt. #1 | | | | |
| 0 | 0.0 | 0.005 | 0.0 | 0.5 |
| 80 | 0.83 | 0.010 | 64.0 | 1.0 |
| Expt. #2 | | | | |
| 0 | 0.0 | 0.008 | 0.0 | 1.0 |
| 80 | 0.59 | 0.013 | 45.0 | 1.6 |

As can be seen from the above table, the sucrose was at least 98 percent contained over the 80 hour period in both the experiments which indicates that the emulsions remained substantially intact. The controlled release of sodium salicylate was demonstrated by releasing 64 and 45 percent respectively of the maximum possible amounts over the 80 hour period.

The selection of the interior phase of the emulsions of the instant invention is dependent on their intended use. For example, toxins present in the GI tract may be removed by trapping in the internal phase of the emulsion, i.e. conversion of a toxin which can permeate the exterior phase of the emulsion to an impermeable form. Toxins may also be converted, in the interior phase, to an innocuous form, or alternatively to a form which may be subsequently trapped. An example of this technique is the conversion of urea, by use of urease, into carbon dioxide, which may be exhaled, and ammonia, which may be trapped by an encapsulated strong acid.

The various toxins which may be removed from the GI tract by trapping in the interior phase of the compositions of the instant invention include:

TABLE 2

Toxin Removal with Reagents Encapsultated in Liquid Membranes

| Toxin | Reagents |
|---|---|
| Ammonia | Acid - preferably hydrochloric, sulfuric or citric |
| Phenol | Base - preferably sodium hydroxide. |
| Phosphate | Calcium Salts - preferably a combination of calcium chloride and calcium hydroxide. |
| Lactic Acid | Base - preferably sodium hydroxide. |
| Iron | Base - preferably sodium hydroxide. |
| Copper | Sulfide - preferably sodium sulfide. |
| Silver | Sulfide - preferably sodium sulfide. |

TABLE 2-continued

Toxin Removal with Reagents Encapsultated in Liquid Membranes

| Toxin | Reagents |
|---|---|
| Mercury | Sulfide - preferably sodium sulfide. |

Examples of using the instant invention to convert materials present in the GI tract into useful products include:

(1) The use of liquid membrane encapsulated amylase (an enzyme for the hydrolysis of starches for the digestion of starches), (2) The use of liquid membrane encapsulated lipase (an enzyme for the hydrolysis of triglycerides) for the digestion of triglycerides.

(3) The use of liquid membrane encapsulated lactase to help young children hydrolyze lactose, (4) The use of liquid membrane encapsulated mixed pancreatic enzymes to promote the digestion and utilization of proteins in children with cystic fibrosis.

Other examples of using the compositions of the instant invention as reactors, wherein materials which are not capable of being trapped by reaction or adsorption in the interior phase of emulsions of the instant invention are converted into products which can be so trapped or adsorbed, include converting glucose to gluconic acid, and, lactose to lactic acid.

The compositions of the instant invention may be utilized as slow release medicinals. For example, sodium Salicylate, as described above, Trimethaphan Camphorsulfonate, Trimethadione, Metronidazole and Penicillin O, particularly the water soluble potassium salt, or aspirin or derivatives thereof.

In the preparation of products of this sort, the emulsion is designed so that the medicinal is only slightly soluble in the exterior phase so as to provide permeation of the medicinal through the exterior phase into the GI tract over a period of time. In general, emulsions of this sort are designed so that the medicinal is soluble in the external phase from about 0.0001 wt. % to about 10 wt. % at 37° C.

In carrying out the process of the instant invention, the interior phase is selected according to the above criteria to enable the skilled artisan to carry out the desired operations. For example, when it is desired to provide a composition for the removal of ammonia in the GI tract, an internal phase comprising a 10 normal aqueous hydrochloric acid solution is emulsified in a hydrocarbon solution containing a nonionic surfactant along with a strengthening agent for the hydrocarbon phase. This strengthening agent as will be further described below, is utilized to provide emulsions which do not break during passage to the GI tract since it would be quite evident to the skilled artisan that the advantages of the instant invention will not be obtained with emulsions that are not stable during passage through the GI tract. The aqueous and hydrocarbon mixture is emulsified under vigorous agitation to form a stable emulsion. In this procedure, the aqueous phase is added slowly to the hydrocarbon oil-soluble surfactant and strengthening agent solution over a period of time to form an oil continuous emulsion. This emulsion may be passed directly by ingestion through the GI tract; however, in the preferred embodiment, this emulsion will be mixed under conditions of low agitation with water to provide a three-phase system. This three-phase system may be then ingested and subsequently passed through the GI tract. This particular emulsion will pass through the stomach into the intestines wherein ammonia present therein will permeate through the exterior phase of the emulsion, i.e., the hydrocarbon continuous phase, into the aqueous hydrochloric acid phase wherein the ammonia will be converted to ammonium chloride which is impermeable and thus trapped in the interior phase. The emulsion, being stable during passage through the GI tract, then will be passed out of the human body carrying the ammonia trapped in the interior phase along with it.

The following are other specific embodiments of the instant invention, however, there is no intention to be bound by these embodiments since variations which would be obvious to the skilled artisan may be made.

EXAMPLE 2—Ammonia Removal

Liquid membrane encapsulation that is utilizing the exterior phase of an emulsion as a membrane allows one to use effective ionic reagents such as hydrochloric acid, which cannot be used with other encapsulation methods. A hydrocarbon base liquid membrane is used. The ionic barrier character of this membrane prevents the hydrogen and chlorine ions of this totally ionized strong acid from penetrating the membrane to the bulk fluid (which would be the gut fluid in this application). The species to be removed, ammonia, always exists in equilibrium with the ammonium ion ($NH_3 + H^+ \rightleftharpoons NH_4^+$). Which form is dominant depends on the pH. Ammonia, the molecular species $NH_3$, which exists at gut pH's, can readily penetrate the liquid membrane to contact the hydrochloric acid reagent. At the very low pH of the encapsulated hydrochloric acid, the molecular ammonia which has moved through the liquid membrane is converted to ammonium ($NH_4^+$). This ionic species is prevented from transferring back out by the ion barrier properties of this liquid membrane.

The liquid membrane encapsulated hydrochloric acid is shown to be effective experimentally. For any reagent system to be effective in the gut, it must remove ammonia from the very low concentrations which are found in the gut. Tests with liquid membrane encapsulated hydrochloric acid reduced the ammonia concentration of a solution down to less than 3 mg %, i.e. 3 mg per 100 cc's.

In addition to removing ammonia to low levels, small reagent volumes are highly desirable. This could be accomplished by using liquid membrane encapsulated concentrated, 10 normal, hydrochloric acid. In this experiment, the liquid membrane oil phase was made from:

2 gm of Sorbitan monooleate
0.5 gm of a high molecular weight polyamine with the structure

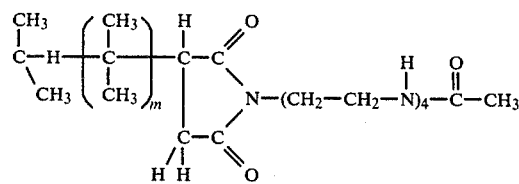

4.5 gm of a polyisobutylene with an ave. molecular weight of about 900.

93.0 gm of an isoparaffinic lubricating oil stock with a viscosity at 100° F. of about 600 Saybolt Universal seconds.

100 gm of oil phase total

To the above 100 gms of oil phase, 50 gm of 10N hydrochloric acid was added in a progression of drops with vigorous agitation to form an emulsion. One gram of this emulsion was added to 100 gms of dilute ammonia solution in a beaker. The combination was stirred with a propeller at a very slow 50 rpm to give very mild agitation. This agitation is probably milder than naturally occurs in the gut. As too mild an agitation can produce slow removal, it was a severe test. The very encouraging rapid removal of ammonia obtained is shown below in Table 3.

TABLE 3

| Ammonia Removal by Liquid Membranes | |
|---|---|
| Contract Time (Hours) | Ammonia Concn. in Bulk Phase (mg%) |
| 0 | 26 |
| ½ | 21 |
| 2 | 10 |
| 24 | 6 |

Note that the ammonia level was reduced from 26 mg % to 10 mg % in the first two hours of this gentle contacting. The level dropped to 6 mg % in 24 hours. The effectiveness of ammonia removal was also quite encouraging. Based on the ammonia removal achieved in this experiment with 1 gm of liquid membrane encapsulated reagent, the quantity required to remove all of the nitrogen from 12 gm/day of urea was calculated. Only 300 cc of emulsion per day is required. The use of a liquid membrane suspension, i.e. the above-described emulsion suspended in an aqueous phase, wherein 40 volume percent of the emulsion was concentrated hydrochloric acid, would lower the requirements to 100 cc's for removal of all the urea nitrogen.

The liquid membrane must also function in gut fluid. To test this, a synthetic gut fluid was prepared. The synthetic gut fluid was made with 0.5 wt. % NaCl to simulate salt concentration, buffered with 0.4 wt. % $NaHCO_3$ to hold the proper pH and contained 0.8 wt. % egg albumin to simulate protein content. The same type of experiments described above were performed. The results, below in Table 4, show quite clearly that the liquid membrane encapsulated hydrochloric acid removes ammonia from synthetic gut fluid.

TABLE 4

| Ammonia Removal from Synthetic Gut Fluid | |
|---|---|
| Contact Time (Hours) | Ammonia Concn. in Synthetic Gut Fluid (mg%) |
| 0 | 38 |
| 1 | 19 |
| 24 | 20 |
| 48 | 13 |

Another quite interesting observation was made when contacting the above-described emulsion with synthetic gut fluid. The stability was enhanced. This may be a result of protein adsorption on the suspended emulsion droplets. The enhanced stability in gut fluid may play an important role in the in vivo emulsion stability discussed below.

The hydrochloric acid reagent could be replaced with citric acid, or any other acid capable of neutralizing ammonia, in the above example.

EXAMPLE 3—Urease Encapsulation

The approach discussed above concerned the removal of ammonia which had been generated from urea by the enzyme urease. Substantial urease activity in the gut has been established by the literature. However it has not been conclusively proved that there is sufficient urease activity to convert all the urea that must be removed each day. It might be necessary to introduce more urease activity to the gut. Simple injection of unencapsulated urease would not likely be effective as the low pH of the stomach would denature much of the enzyme. Therefore, the encapsulation of urease was tested in a neutral solution by ion excluding liquid membrane. The ion exclusion nature of the liquid membrane would prevent the hydrogen ions present at the low pH of the stomach from penetrating the membrane and damaging the urease. The molecular species urea, however, could readily transfer through the membrane where it would be hydrolyzed to ammonia and carbon dioxide. The carbon dioxide, again a molecular species, could transfer back out through the membrane. The 9 grams per day of carbon dioxide produced from 12 gms per day of urea could readily be handled by the lungs. The ammonia produced by the urease encapsulated in the liquid membrane could transfer out through the liquid membrane. This occurs because the phase encapsulated in these membranes is near neutral. At near neutral pH's the main species is unionized ammonia which can transfer out of the ion barrier liquid membrane. The ammonia leaving the encapsulated urease may then be removed from the gut fluid by the previously discussed ammonia trapping.

The system described above was experimentally checked for the transfer of reactant and products into and out of the urease containing interior phase as well as the activity and effective isolation of the urease. A liquid membrane forming emulsion was made by dissolving 0.046 wt. % urease in water and adding it dropwise into an oil phase under vigorous agitation. The oil phase consisted of:

2 wt. % Sorbitan monooleate
3 wt. % High molecular weight polyamine with the structure

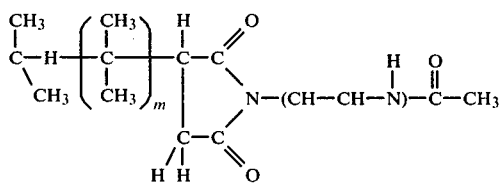

95 wt. % Isoparaffinic lubricating oil stock with a viscosity at 100° F. of about 100 Saybolt Universal Seconds.

In the final emulsion, the weight ratio of the urease solution to oil phase was 0.82. Two ml. of the above emulsion was added to 30 ml of a solution containing 0.43 Molar Urea, 0.1 Molar NaCl, 0.0008 Molar phosphate buffer and containing 0.1μ of Clelands reagent. Moderate stirring was used to disperse the emulsion in liquid membrane form. The pH of this bulk area containing solution was held at 6.7±0.05 by an automatic titrator which neutralized the excess product ammonia with 10 normal HCl. (At the 6.7 pH one-half of the ammonia produced is in excess over the quantity forming bicarbonate with the carbon dioxide). In these experiments, the quantity of HCl required to balance the excess product ammonia was recorded with time. The liquid membranes were removed during the experiments and reintroduced at a later time.

Note that the increasing HCl required initially indicates that the enzyme catalyzed reaction as well as the transfer of urea into and carbon dioxide and ammonia out of the urease containing internal phase was occurring. When the emulsions were removed, the reaction stopped. This shows that the enzyme did not penetrate the liquid membrane to the bulk phase and that the initial measured reaction rate was that produced by liquid membrane encapsulated urease. Reintroduction of the emulsion started the reaction again.

The formation of ammonia in these experiments was also confirmed by independent specific analysis of ammonia built up with time.

The rates of reaction were about 1/50 of those measured under similar conditions with freshly dissolved urease in the unprotected bulk phase. This is a reasonable rate and the reduction from bulk phase includes the effects of several factors. The denaturation of the enzyme during encapsulation, and any limitations in transferring material through the liquid membrane or inside the encapsulated phase would all decrease the measured urease activity.

EXAMPLE 4—Phosphate Removal

Since the phosphate ion is difficult to remove by hemodialysis an adjunct method of removal would be particularly useful. The reagent system selected for encapsulation is suggested by nature. Excess phosphate in the body can precipitate with calcium in non-physiologic modes. The system selected encapsulates calcium salts in an anion transferring liquid membrane. The cation calcium is retained in the liquid membrane. The anion phosphate transfers through the liquid membrane to react with the calcium forming the calcium phosphate precipitate which is trapped in the interior emulsion phase.

This system was experimentally tested using a 15 weight percent CaCl₂ and a 5 weight percent Ca(OH)₂ reagent encapsulated in an anion transporting liquid membrane. The oil phase of this emulsion consisted of 95 wt. % Isoparaffin lubricating oil stock with a viscosity at 100° F. of about 100 Saybolt Universal Seconds
2 wt. % Mixture of primary and secondary amines with a molecular weight range of 353 to 393 which has an ion exchange capacity of about 2.7 meg/gm., e.g. Amberlite LA 2 available from Rohm and Haas.
2 wt. % Polyamine with a molecular weight of about 2000 with the structure

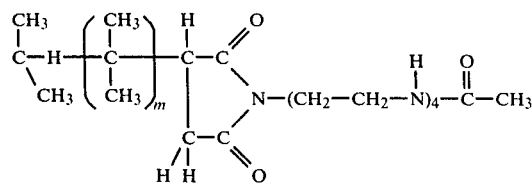

1 wt. % Sorbitan monooleate

The aqueous phase was added to the oil to form 33 wt. % of the total aqueous plus oil phase with vigorous agitation. This emulsion (281 gms) was then dispersed in a phosphate solution (500 gm). The rapid phosphate removal is shown in Table 5 below:

TABLE 5

| Rapid Phosphate Removal | |
|---|---|
| Time (min.) | Phosphate (wt. %) |
| 0 | 0.273 |
| 2 | 0.123 |
| 5 | 0.073 |
| 18 | 0.016 |
| 44 | 0.004 |

Assuming the removal of all the phosphate ion (½ gms/day as phosphorous) was desired the quantity of liquid membrane suspension, i.e. the emulsion suspended in an aqueous phase, required can be calculated. Based on the above reagent concentration and the reagent occupying 40 volume percent of a liquid membrane suspension, 57 cc would be required per day.

EXAMPLE 5—In Vivo Stability of Emulsions

Emulsions that are used to treat chronic uremia by ingestion must be stable throughout the gastrointestinal tract. As a critical test of stability, high doses of a poison were encapsulated in an emulsion to see if the stability of the liquid membrane barrier was sufficient to prevent killing test animals. The poison selected was sodium cyanide at 10 times the lethal dose (10×LD 50). The liquid membrane formulation was the same ion excluding formulation which was used in removing ammonia from solution and synthetic gut fluid. Wistar-strain, albino rats were used for this study. In addition to the rats used to determine the LD 50 of this population, three groups of 10 rats were used. One group received distilled water encapsulated in the liquid membrane. A second group received 10 times the lethal dose of sodium cyanide encapsulated in the liquid membrane. The encapsulated aqueous phase was 0.5 wt. % sodium cyanide. This sodium cyanide solution was emulsified at a 33 wt. % level in the same oil phase composition as usual in the ammonia removal examples. This emulsion was then suspended in an equal volume of water to form liquid membrane prior to administration. In the third group, the hydrocarbon solution and the sodium cyanide solution were introduced as separate liquids so there were no liquid membranes. All the materials were administered by oral intubation. The results are summarized below in Table 6.

TABLE 6

| | LIQUID MEMBRANE STABILITY IN VIVO | | |
|---|---|---|---|
| Time After Administration | Group 1 Liquid Membrane Encapsulated H$_2$O | Group 2 Liquid Membrane Encapsulated HCN | Group 3 Same as Group 2 Not Encapsulated |
| 5 min. | active, feeding | active, feeding | all knocked down |
| 30 min. | active, feeding | active, feeding | all dead |
| 1 hr. | active, feeding | active, feeding | |
| 2 hr. | active, feeding | active, feeding | |
| 1 day | active, feeding | active, feeding | |
| 7 days | active, feeding | active, feeding | |

Additionally, the rats administered 10 times the lethal dosage of NaCN in the emulsion were observed to have no signs of toxicity of pharmocologic effects throughout the test. It was concluded that the emulsions of the instant invention have good stability in vivo.

What is claimed is:

1. A method for removing a toxin from the gastrointestinal tract which comprises providing an emulsion in said gastrointestinal tract, said emulsion comprising an interior phase surrounded by an exterior phase, said exterior phase being immiscible with the aqueous environment of said gastrointestinal tract and permeable to said toxin, said exterior phase comprising an oil-soluble surfactant component and an oil component, said oil-soluble surfactant component and said oil component are harmless to the human body, said oil-soluble surfactant component being present in said exterior phase from about 0.01 wt. % up to the solubility limit of said surfactant in said exterior phase but not more than 90 wt. % of said exterior phase, said oil component having a viscosity between about 2 and about 1,000 centistokes at normal body temperature and is selected from the group consisting of vegetable oils and animal fats that are heavily hydrogenated to contain at least 10% more hydrogen then normal saturation, per fluorinated hydrocarbons, silicone fluids containing the repeating unit

and hydrocarbon oils refined to remove toxic ingredients and comprising molecular weights up to 1,000, selected from the group consisting of paraffins, isoparaffins, naphthenes, and aromatics and said interior phase being immiscible with said exterior phase and comprises a reactant capable of converting said toxin into a nonpermeable form, said emulsion being further characterized as being stable in said gastrointestinal tract, whereby said toxin permeates the exterior phase of said emulsion into said interior phase and is converted into a nonpermeable form.

2. The process of claim 1 wherein said emulsion is suspended in a liquid which is not harmful to the human body and said liquid is immiscible with said exterior phase of said emulsion.

3. The process of claim 2 wherein a strengthening agent is included in said emulsion to improve said emulsion's stability.

4. The process of claim 2 wherein said oil component is a hydrocarbon oil refined to remove toxic ingredients and comprises molecular weights up to 1,000, selected from the group consisting of paraffins, isoparaffins, naphthenes, and aromatics.

5. The process of claim 4 wherein a strengthening agent is included in said emulsion's exterior phase from about 2 wt. % up to the solubility limit of said strengthening agent in said exterior phase.

6. The process of claim 5 wherein said strengthening agent is included in said emulsions exterior phase from about 2 wt. % up to the solubility limit of said strengthening agent in said exterior phase but not more than 5 wt. % of said exterior phase.

7. The process of claim 4 wherein said oil-soluble surfactant component is present in said exterior phase from about 0.01 wt. % up to the solubility limit of said surfactant in said exterior phase but not more than 10 wt. % of said exterior phase.

8. The process of claim 7 wherein a strengthening agent is included in said emulsion's exterior phase from about 2 wt. % up to the solubility limit of said strengthening agent in said exterior phase.

9. The process of claim 8 wherein said toxin is ammonia.

10. The process of claim 9 wherein said reactant is an acid.

11. The process of claim 10 wherein said acid is hydrochloric acid.

12. The process of claim 8 wherein said strengthening agent comprises a polyamine derivative having the general formula:

$$H-\underset{CH_3}{\underset{|}{\overset{CH_3}{\overset{|}{C}}}}-\left(\underset{CH_3}{\underset{|}{\overset{CH_3}{\overset{|}{C}}}}\right)_n-\underset{\underset{H-C-C}{\underset{|}{\overset{H}{\overset{|}{C}}}}\underset{\|}{\overset{O}{}}}{\overset{H}{\overset{|}{C}}-\overset{O}{\overset{\|}{C}}}\diagdown N-\left[\begin{array}{c}H\ H\ H\\ |\ |\ |\\ C-C-N\\ |\ |\\ H\ H\end{array}\right]_x y$$

wherein n varies from 10 to 60, x varies from 3 to 10, and y is selected from the group consisting of hydrogen and oxygen-containing hydrocarbyl radicals having up to 10 carbons.

13. The process of claim 12 wherein said oil-soluble surfactant component comprises said polyamine derivative.

14. A method for removing a toxin from the gastrointestinal tract which comprises providing an emulsion in said gastrointestinal tract, said emulsion comprising an interior phase surrounded by an exterior phase, said exterior phase being immiscible with the aqueous environment of said gastrointestinal tract and permeable to said toxin, said exterior phase comprising an oil-soluble surfactant component and an oil component, said oil-soluble surfactant component and said oil component are harmless to the human body, said oil-soluble surfactant component being present in said exterior phase from about 0.01 wt. % up to the solubility limit of said surfactant in said exterior phase but not more than 90 wt. % of said exterior phase, said oil component having a viscosity between about 2 and about 1,000 centistokes at normal body temperature and is selected from the group consisting of vegetable oils and animal fats that are heavily hydrogenated to contain at least 10% more hydrogen than normal saturation, perfluorinated hydrocarbons, silicone fluids containing the repeating unit $$-\underset{CH_3}{\underset{|}{\overset{CH_3}{\overset{|}{Si}}}}-O$$

and hydrocarbon oils refined to remove toxic ingredients and comprising molecular weights up to 1,000, selected from the group consisting of paraffins, isoparaffins, naphthenes and aromatics, and said interior phase being immiscible with said exterior phase and comprises a catalyst which is insoluble in said exterior phase and capable of converting said toxin into a nontoxin, said emulsion being further characterized as being stable in said gastrointestinal tract, whereby said toxin permeates said exterior phase and is converted into a nontoxin in said interior phase.

15. The process of claim 14 wherein said emulsion is suspended in a liquid which is not harmful to the human body and said liquid is immiscible with said exterior phase of said emulsion.

16. The process of claim 15 wherein a strengthening agent is included in said emulsion to improve said emulsion's stability.

17. The process of claim 16 wherein said nontoxin permeates from the interior phase of said emulsion into said gastrointestinal tract.

18. The process of claim 17 wherein said interior phase is aqueous and comprises an enzyme.

19. The process of claim 15 wherein said oil component is a hydrocarbon oil refined to remove toxic ingredients and comprises molecular weights up to 1,000, selected from the group consisting of paraffins, isoparaffins, naphthenes and aromatics.

20. The process of claim 19 wherein a strengthening agent is included in said emulsion's exterior phase from about 2 wt. % up to the solubility limit of said strengthening agent in said exterior phase.

21. The process of claim 20 wherein said strengthening agent is included in said emulsions exterior phase from about 2 wt. % up to the solubility limit of said strengthening agent in said exterior phase, but not more than 5 wt. % of said exterior phase.

22. The process of claim 19 wherein said oil-soluble surfactant component is present in said exterior phase from about 0.01 wt. % up to the solubility limit of said surfactant in said exterior phase but not more than 10 wt. % of said exterior phase.

23. The process of claim 22 wherein a strengthening agent is included in said emulsion's exterior phase from about 2 wt. % up to the solubility limit of said strengthening agent in said exterior phase.

24. The process of claim 23 wherein said strengthening agent comprises a polyamine derivative having the general formula:

$$H-\underset{CH_3}{\underset{|}{\overset{CH_3}{\overset{|}{C}}}}-\left(\underset{CH_3}{\underset{|}{\overset{CH_3}{\overset{|}{C}}}}\right)_n-\underset{\underset{H-C-C}{\underset{|}{\overset{H}{\overset{|}{C}}}}\underset{\|}{\overset{O}{}}}{\overset{H}{\overset{|}{C}}-\overset{O}{\overset{\|}{C}}}\diagdown N-\left[\begin{array}{c}H\ H\ H\\ |\ |\ |\\ C-C-N\\ |\ |\\ H\ H\end{array}\right]_x y$$

wherein n varies from 10 to 60, x varies from 3 to 10, and y is selected from the group consisting of hydrogen and oxygen-containing hydrocarbyl radicals having up to 10 carbons.

25. The process of claim 24 wherein said oil-soluble surfactant component comprises said polyamine derivative.

26. A method for removing a toxin from the gastrointestinal tract which comprises providing in said tract a first emulsion, said emulsion comprising an interior phase surrounded by an exterior phase, said exterior phase being immiscible with the aqueous environment of said gastrointestinal tract and permeable to said toxin, said exterior phase comprising an oil-soluble surfactant component and an oil component, said oil-soluble surfactant component and said oil component are harmless to the human body, said oil-soluble surfactant component being present in said exterior phase from about 0.01 wt. % up to the solubility limit of said surfactant in said exterior phase but not more than 90 wt. % of said exterior phase, said oil component having a viscosity between about 2 and about 1,000 centistokes at normal body temperature and is selected from the group consisting of vegetable oils and animal fats that are heavily hydrogenated to contain at least 10% more hydrogen than normal saturation, perfluorinated hydrocarbons, silicone fluids containing the repeating unit

and hydrocarbon oils refined to remove toxic ingredients and comprising molecular weights up to 1,000, selected from the group consisting of paraffins, isoparaffins, naphthenes and aromatics, and said interior phase being immiscible with said exterior phase and comprises a catalyst which is insoluble in said exterior phase and capable of converting said toxin into a reaction product, providing a second emulsion in said tract, said second emulsion comprising a second interior phase surrounded by a second exterior phase, said second exterior phase being immiscible with the aqueous environment of said gastrointestinal tract and permeable to said reaction product, said second exterior phase comprising an oil-soluble surfactant component and an oil component, said oil-soluble surfactant component and said oil component are harmless to the human body, said oil-soluble surfactant component being present in said exterior phase from about 0.01 wt. % up to the solubility limit of said surfactant in said exterior phase but not more than 90 wt. % of said exterior phase, said oil component having a viscosity between about 2 and about 1,000 centistokes at normal body temperature and is selected from the group consisting of vegetable oils and animal fats that are heavily hydrogenated to contain at least 10% more hydrogen than normal saturation, perfluorinated hydrocarbons, silicone fluids containing the repeating unit and hydrocarbon oils refined to remove toxic ingredients and comprising molecular weights up to 1,000, selected from the group consisting of paraffins, isoparaffins, naphthenes and aromatics, and said interior phase being immiscible with said exterior phase and comprises a reactant which is capable of converting said reaction product into a nonpermeable form, whereby said toxin permeates said exterior phase of the first emulsion and is converted into said reaction product in said first emulsion's interior phase, said reaction product permeates from the interior phase of said first emulsion into said gastrointestinal tract and said reaction product permeates said second exterior phase and is converted to said nonpermeable form in said second interior phase wherein said first and second emulsions are further characterized as being stable in said gastrointestinal tract.

27. The process of claim 26 wherein said first and second emulsions are suspended in a liquid which is not harmful to the human body and said liquid is immiscible with said exterior phase of said first emulsion.

28. The process of claim 27 wherein a strengthening agent is included in said first and second emulsion to improve said emulsions' stabilities.

29. The process of claim 28 wherein the interior phase of said first emulsion is aqueous and contains urease as the catalyst and said toxin is urea.

30. The process of claim 28 wherein said strengthening agent of said first emulsion's exterior phase and said second emulsion's exterior phase comprise a polyamine derivative having the general formula:

wherein n varies from 10 to 60, x varies from 3 to 10, and y is selected from the group consisting of hydrogen and oxygen-containing hydrocarbyl radicals having up to 10 carbons.

31. The process of claim 30 wherein said oil-soluble surfactant component comprises said polyamine derivative.

32. A process for the converting of undigested compositions present in the gastrointestinal tract to digested compositions which comprises providing an emulsion in said gastrointestinal tract which comprises an interior phase surrounded by an exterior phase, said exterior phase being immiscible with the aqueous environment of said gastrointestinal tract and permeable to said undigested compositions, said exterior phase comprising an oil-soluble surfactant component and an oil component, said oil compound and said oil-soluble surfactant component are harmless to the human body, and said oil component having a viscosity between 2 and 1,000 centistokes at normal body temperature, and is selected from the group consisting of vegetable oils and animal fats that are heavily hydrogenated to contain at least 10% more hydrogen than at normal saturation, perfluorinated hydrocarbons, silicone fluids containing the repeating unit and hydrocarbon oils refined to remove toxic ingredients and comprising molecular weights up to 1,000, selected from the group consisting of paraffins, isoparaffins, naphthenes and aromatics, and said interior phase being immiscible with said exterior phase and comprises a catalyst capable of converting said undigested composition into said digested composition, said emulsion being further characterized as being stable in said gastrointestinal tract, whereby said undigested composition permeates the exterior phase of said emulsion into said interior phase where it is converted into said digested composition.

33. The process of claim 32 wherein said emulsion is suspended in a liquid which is not harmful to the human body and said liquid is immiscible with said exterior phase of said emulsion.

34. The process of claim 33 wherein a strengthening agent is included in said emulsion to improve said emulsion's stability.

35. The process of claim 33 wherein said oil component is a hydrocarbon oil refined to remove toxic ingredients and comprises molecular weights up to 1,000, selected from the group consisting of paraffins, isoparaffins, naphthenes and aromatics.

36. The process of claim 35 wherein a strengthening agent is included in said emulsion's exterior phase from about 2 wt. % up to the limit of said strengthening agent in said exterior phase.

37. The process of claim 36 wherein said strengthening agent is included in said emulsion's exterior phase from about 2 wt. % up to the solubility limit of said strengthening agent in said exterior phase but not more than 5 wt. % of said exterior phase.

38. The process of claim 35 wherein said oil-soluble surfactant component is present in said exterior phase from about 0.01 wt. % up to the solubility limit of said surfactant in said exterior phase but not more than 10 wt. % of said exterior phase.

39. The process of claim 38 wherein a strengthening agent is included in said emulsion's exterior phase from about 2 wt. % up to the limit of said strengthening agent in said exterior phase.

40. The process of claim 39 wherein said interior phase is aqueous, said catalyst is amylase, and said undigested composition is a starch.

41. The process of claim 39 wherein said interior phase is aqueous, said catalyst is lipase and said undigested composition is selected from the group of triglycerides.

42. The process of claim 39 wherein said interior phase is aqueous, said catalyst is lactase and said undigested composition is lactose.

43. The process of claim 39 wherein said interior phase is aqueous, said undigested composition is a protein and said catalyst is selected from the group consisting of pancreatic enzymes and mixtures thereof.

44. The process of claim 39 wherein said strengthening agent comprises a polyamine derivative having the general formula:

$$H-\underset{\underset{CH_3}{|}}{\overset{\overset{CH_3}{|}}{C}}-\left(\underset{\underset{CH_3}{|}}{\overset{\overset{CH_3}{|}}{C}}\right)_n-\underset{\underset{H}{|}}{\overset{\overset{H}{|}}{C}}-\underset{}{\overset{\overset{O}{\|}}{C}}\underset{H-\underset{\underset{H}{|}}{\overset{\overset{}{}}{C}}-\underset{}{\overset{\overset{O}{\|}}{C}}}{\overset{}{\diagup}}N-\left[\begin{array}{c}H\ H\ H\\|\ |\ |\\-C-C-N-\\|\ |\\H\ H\end{array}\right]_x-y$$

wherein n varies from 10 to 60, x varies from 3 to 10, and y is selected from the group consisting of hydrogen and oxygen-containing hydrocarbyl radicals having up to 10 carbons.

45. The process of claim 44 wherein said oil-soluble surfactant component comprises said polyamine derivative.

46. An emulsion useful in removing a toxin from the gastrointestinal tract and which is characterized as being stable in said gastrointestinal tract, which comprises an interior phase surrounded by an exterior phase, said exterior phase is immiscible with the aqueous environment of said gastrointestinal tract and permeable to said toxin, said exterior phase comprises an oil-soluble surfactant component and an oil component, said oil-soluble surfactant component and said oil component are harmless to the human body, said oil-soluble surfactant component is present in said exterior phase from about 0.01 wt. % up to the solubility limit of said surfactant in said exterior phase but not more than 90 wt. % of said exterior phase, said oil component has a viscosity between about 2 and about 1,000 centistokes at normal body temperature and is selected from the group consisting of vegetable oils and animal fats that are heavily hydrogenated to contain at least 10% more hydrogen than normal saturation, perfluorinated hydrocarbons, silicone fluids containing the repeating unit $$-\underset{\underset{CH_3}{|}}{\overset{\overset{CH_3}{|}}{Si}}-O$$

and hydrocarbon oils refined to remove toxic ingredients and comprises molecular weights up to 1,000, selected from the group consisting of paraffins, isoparaffins, naphthenes, and aromatics and said interior comprises a reactant capable of converting said toxin into a nonpermeable form.

47. The emulsion of claim 46 wherein said emulsion is suspended in a liquid which is not harmful to the human body and said liquid is immiscible with said exterior phase of said emulsion.

48. The emulsion of claim 47 wherein a strengthening agent is included in said emulsion to improve said emulsion's stability.

49. The emulsion of claim 47 wherein said oil component is a hydrocarbon oil refined to remove toxic ingredients and comprises molecular weights up to 1,000, selected from the group consisting of paraffins, isoparaffins, naphthenes, and aromatics.

50. The emulsion of claim 49 wherein a strengthening agent is included in said emulsion's exterior phase from about 2 wt. % up to the solubility limit of said strengthening agent in said exterior phase.

51. The emulsion of claim 50 wherein said strengthening agent is included in said emulsion's exterior phase from about 2 wt. % up to the solubility limit of strengthening agent in said exterior phase but not more than 5 wt. % of said exterior phase.

52. The emulsion of claim 49 wherein said oil-soluble surfactant component is present in said exterior phase from about 0.01 wt. % up to the solubility limit of said surfactant in said exterior phase but not more than 10 wt. % of said exterior phase.

53. The emulsion of claim 52 wherein a strengthening agent is included in said emulsion's exterior phase from about 2 wt. % up to the solubility limit of said strengthening agent in said exterior phase.

54. The emulsion of claim 53 wherein said toxin is ammonia.

55. The emulsion of claim 54 wherein said reactant is an acid.

56. The emulsion of claim 53 wherein said strengthening agent comprises a polyamine derivative having the general formula:

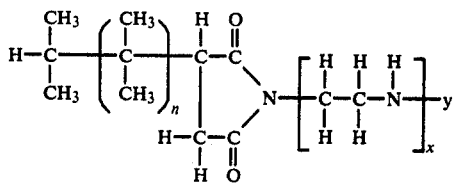

wherein n varies from 10 to 60, x varies from 3 to 10, and y is selected from the group consisting of hydrogen and oxygen-containing hydrocarbyl radicals having up to 10 carbons.

57. The emulsion of claim 56 wherein said oil-soluble surfactant component comprises said polyamine derivative.

58. An emulsion useful for converting a toxin present in the gastrointestinal tract into a nontoxin which emulsion is characterized as being stable in said gastrointestinal tract, said emulsion comprising an interior phase surrounded by an exterior phase, said exterior phase is immiscible with the aqueous environment of said gastrointestinal tract and permeable to said toxin, said exterior phase comprises an oil-soluble surfactant component and an oil-component, said oil-soluble surfactant component and said oil component are harmless to the human body, said oil-soluble surfactant component is present in said exterior phase from about 0.01 wt. % up to the solubility limit of said surfactant in said exterior phase but not more than 90 wt. % of said exterior phase, said oil component has a viscosity between about 2 and about 1,000 centistokes at normal body temperature and is selected from the group consisting of vegetable oils and animal fats that are heavily hydrogenated to contain at least 10% more hydrogen than normal saturation, perfluorinated hydrocarbons, silicone fluids containing the repeating unit and hydrocarbon oils refined to remove toxic ingredients and comprising molecular weights up to 1,000, selected from the group consisting of paraffins, isoparaffins, naphthenes and aromatics, and said interior phase being immiscible with said exterior phase and comprises a catalyst which is insoluble in said exterior phase and capable of converting said toxin into a nontoxin.

59. The emulsion of claim 58 wherein said emulsion is suspended in a liquid which is not harmful to the human body and said liquid is immiscible with said exterior phase of said emulsion.

60. The emulsion of claim 59 wherein a strengthening agent is included in said emulsion to improve said emulsion's stability.

61. The emulsion of claim 60 wherein said interior phase is aqueous and comprises an enzyme.

62. The emulsion of claim 59 wherein said oil component is a hydrocarbon oil refined to remove toxic ingredients and comprises molecular weights up to 1,000, selected from the group consisting of paraffins, isoparaffins, naphthenes and aromatics.

63. The emulsion of claim 62 wherein a strengthening agent is included in said emulsion's exterior phase from about 2 wt. % up to the solubility limit of said strengthening agent in said exterior phase.

64. The emulsion of claim 63 wherein said strengthening agent is included in said emulsion's exterior phase from about 2 wt. % up to the solubility limit of said strengthening agent in said exterior phase but not more than 5 wt. % of said exterior phase.

65. The emulsion of claim 62 wherein said oil-soluble surfactant component is present in said exterior phase from about 0.01 wt. % up to the solubility limit of said surfactant in said exterior phase but not more than 10 wt. % of said exterior phase.

66. The emulsion of claim 65 wherein a strengthening agent is included in said emulsion's exterior phase from about 2 wt. % up to the solubility limit of said strengthening agent in said exterior phase.

67. The emulsion of claim 66 wherein said interior phase is aqueous and comprises an enzyme.

68. The emulsion of claim 66 wherein said strengthening agent comprises a polyamine derivative having the general formula:

wherein n varies from 10 to 60, x varies from 3 to 10, and y is selected from the group consisting of hydrogen and oxygen-containing hydrocarbyl radicals having up to 10 carbons.

69. The emulsion of claim 68 wherein said oil-soluble surfactant component comprises said polyamine derivative.

* * * * *